(12) United States Patent
Thurpari et al.

(10) Patent No.: US 7,459,481 B2
(45) Date of Patent: Dec. 2, 2008

(54) STIMULATION OF CPT-1 AS A MEANS TO REDUCE WEIGHT

(75) Inventors: Jagan N. Thurpari, Owings Mills, MD (US); Leslie E. Landree, Baltimore, MD (US); Gabrielle Ronnett, Lutherville, MD (US); Francis P. Kuhajda, Lutherville, MD (US)

(73) Assignee: The Johns Hopkins University School of Medicine Licensing And Technology Development, Baltimore, MD (US)

( * ) Notice: Subject to any disclaimer, the term of this patent is extended or adjusted under 35 U.S.C. 154(b) by 0 days.

(21) Appl. No.: 11/537,968

(22) Filed: Oct. 2, 2006

(65) Prior Publication Data

US 2007/0087037 A1 Apr. 19, 2007

Related U.S. Application Data

(63) Continuation of application No. 10/917,525, filed on Aug. 13, 2004, now abandoned, which is a continuation-in-part of application No. 10/503,605, filed as application No. PCT/US03/03839 on Feb. 10, 2003, now abandoned.

(60) Provisional application No. 60/354,480, filed on Feb. 8, 2002.

(51) Int. Cl.
*A61K 31/34* (2006.01)
*A61K 31/205* (2006.01)

(52) U.S. Cl. ........................... 514/473; 514/556

(58) Field of Classification Search ............... 514/473, 514/556

See application file for complete search history.

(56) References Cited

U.S. PATENT DOCUMENTS 4,434,160 A 2/1984 Jeretin et al.
5,981,575 A 11/1999 Kuhajda et al.
6,413,545 B1 7/2002 Alviar et al.
2004/0161803 A1 8/2004 Corkey

FOREIGN PATENT DOCUMENTS

| WO | WO 99/07388 | 2/1999 |
| WO | WO 01/34145 | 5/2001 |
| WO | WO 01/60174 | 8/2001 |
| WO | WO 02/079501 | 10/2002 |

OTHER PUBLICATIONS

Eaton, et al., Carnitine Palmitoyl Transferase I and the control of myocardial β-oxidation flux Biochemical Society, vol. 29, part 2, p. 245-250, 2001.
Karlic, et al., "Dietary L-carnitine Stimulates Carnitine Acltransferases in the Liver of Aged Rats", The Journal of Histochemistry & Cytochemistry, vol. 50, No. 2, p. 205-212, 2002.
Loftus, et al., "Reduced Food Intake and Body Weight in Mice Treated with Fatty Acid Synthase Inhibitors", Science, vol. 288, p. 2379-2381, Jun. 30, 2002.
Rahman, et al., "Effects of Conjugated Linoleic Acid on Serum Leptin Concentration, Body-Fat Accumulation, and β-Oxidation of Fatty Acid in OLETF Rats", Nutrition, vol. 17, p. 385-390, 2001.

*Primary Examiner*—Raymond J Henley, III
(74) *Attorney, Agent, or Firm*—Hunton & Williams LLP

(57) ABSTRACT

This invention provides methods and compositions for inducing weight loss and maintaining optimum weight comprising administering an agent that stimulates carnitine palmitoyl transferase-1 (CPT-1) activity to the patient in need, including human patients. These methods do not require inhibition of fatty acid synthesis. In particular, this invention provides methods for development of therapeutics that selectively enhance fatty acid oxidation, increase energy production, and reduce adiposity while preserving lean mass, through the pharmacological stimulation of CPT-1 activity. In a preferred mode, the agent is administered in an amount sufficient to increase fatty acid oxidation. In another preferred mode, the agent is administered in an amount sufficient to antagonize malonyl CoA inhibition of CPT-1. In yet another preferred mode, the agent is administered in an amount sufficient to increase malonyl CoA level.

3 Claims, 5 Drawing Sheets

Figure 8 A, B, C
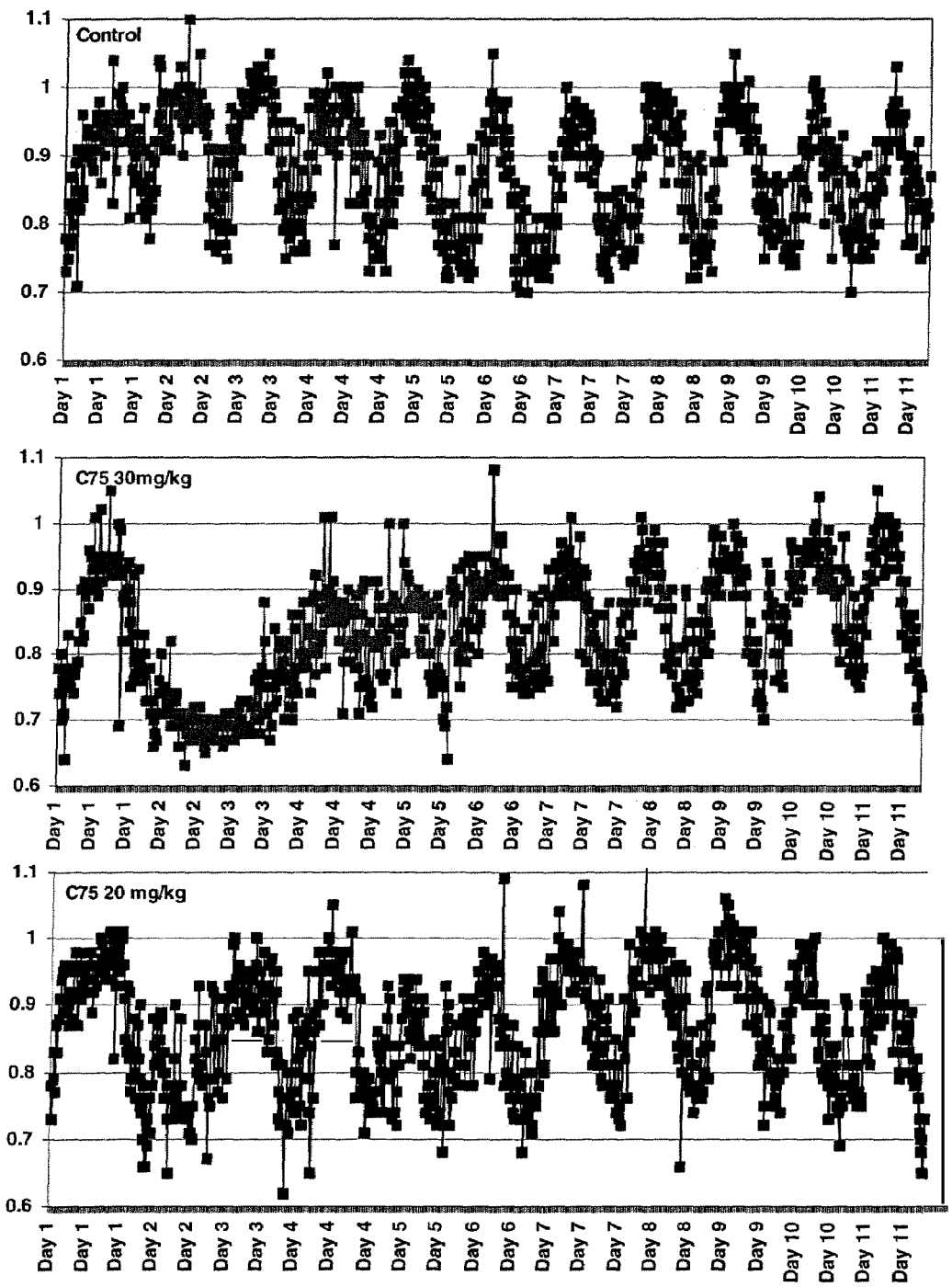

STIMULATION OF CPT-1 AS A MEANS TO REDUCE WEIGHT

CROSS-REFERENCE TO RELATED APPLICATIONS

This application is a continuation of U.S. application Ser. No. 10/917,525, filed Aug. 13, 2004, now abandoned, which is a continuation-in-part of U.S. application Ser. No. 10/503,605, filed Jan. 28, 2005, now abandoned, which claims priority to PCT/US2003/003839, filed Feb. 10, 2003, which claims priority to provisional application No. 60/354,480, filed Feb. 8, 2002.

BACKGROUND

1. Field of the Invention

This invention is directed to a method for development of therapeutics that selectively enhance fatty acid oxidation, increase energy production, and reduce adiposity while preserving lean mass, through the pharmacological stimulation of CPT-1 activity.

2. Review of Related Art

Cerulenin treatment of MCF-7 human breast cancer cells in vitro significantly inhibits fatty acid oxidation, probably through increased levels of malonyl-CoA (Loftus, et al. (2000) *Science,* 288:2379-2381). C75 is a member of a family of α-methylene-γ-butyrolactones which are known inhibitors of fatty acid synthase (FAS) (Kuhajda, et al. (2000) *Proc. Natl. Acad Sci USA,* 97:3450-3454). Treatment of mice with C75 leads to inhibition of hepatic fatty acid synthesis and high levels of malonyl-CoA (Loftus, et al. (2000); Pizer, et al. (2000) *Cancer Res.,* 60:213-218). In the brain, C75 reduces the expression of hypothalamic neuropeptide-Y (NPY) leading to reversible inanition (Loftus, et al, 2000). During in vivo treatment of ob/ob mice with C75 there was profound loss of fat in the liver and peripheral tissues despite the increased levels of hepatic malonyl-CoA (Loftus, et al., 2000).

Malonyl-CoA is a potent inhibitor of fatty acid oxidation through its action as an inhibitor of carnitine-palmitoyl-transferase-1 (CPT-1) (Witters, et al. (1992) *J. Biol. Chem.,* 267:2864-2867). CPT-1 enables the entry of long-chain acyl-CoA's into the mitochondria for fatty acid oxidation. When treated with FAS inhibitors, genetically and diet-induced obese mice undergo a selective and significant loss of adipose tissue despite the high levels of malonyl-CoA induced by FAS inhibition. Since malonyl-CoA is a potent inhibitor of fatty acid oxidation through its inhibition of carnitine palmitoyltransferase-1 (CPT-1, E.C. 2.3.1.21), the rapid and selective loss of adipose tissue was surprising. High systemic levels of malonyl-CoA would be expected to inhibit fatty acid oxidation leading instead to a selective loss of lean mass during C75 induced inanition.

SUMMARY OF THE INVENTION

It is an object of this invention to provide methods and compositions for inducing weight loss and maintaining optimum weight which do not require inhibition of fatty acid synthesis. This and other objects are met by one or more of the following embodiments.

In one embodiment, this invention provides a method of inducing weight loss comprising administering an agent that stimulates carnitine palmitoyl transferase-1 (CPT-1) activity to the patient in need, including human patients. In a preferred mode, the agent is administered in an amount sufficient to increase fatty acid oxidation. In another preferred mode, the agent is administered in an amount sufficient to antagonize malonyl CoA inhibition of CPT-1. In yet another preferred mode, the agent is administered in an amount sufficient to increase malonyl CoA level. In still another preferred mode, upon administration of the agent, malonyl CoA level is not substantially increased. Substantial increase in malonyl CoA level as contemplated herein is equivalent to about one-half the $K_i$ for malonyl CoA inhibition of CPT-1. In yet another preferred mode, the agent which stimulates CPT-1 activity also inhibits fatty acid synthase (FAS). In an alternative mode, FAS is not significantly inhibited. Insignificant inhibition as contemplated herein is less that 15%, preferably less than 10%, and more preferably less than 5% inhibition. Methods for assay of FAS activity are disclosed in U.S. Pat. No. 5,981,575, incorporated herein by reference. In preferred modes of the above embodiments, the agent which stimulates CPT-1 activity is not a compound of formula:

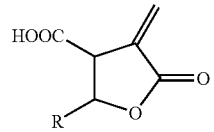

wherein R is a substitute selected from the group consisting of:

(a) saturated linear or branched alkyl groups having 3-18 carbon atoms, (b) unsaturated linear or branched alkyl groups having 3-18 carbon atoms,

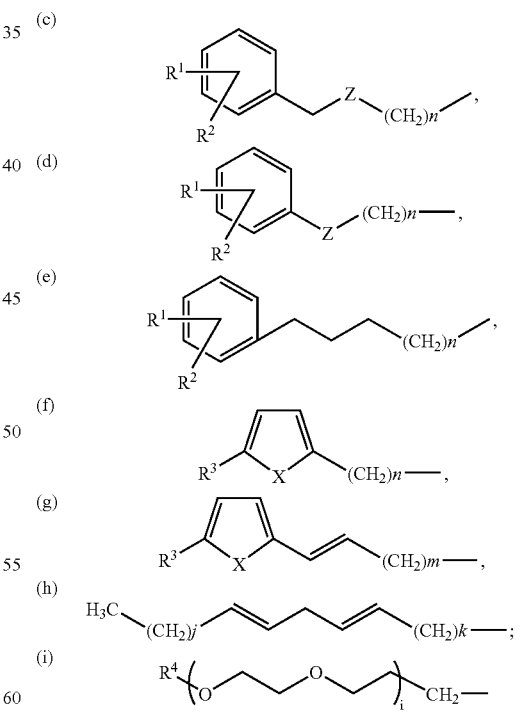

wherein:

$R^1$ and $R^2$, the same or different, are H, $CH_3$, $C_2H_5$, $C_3H_7$, $C_4H_9$, $CF_3$, $OCH_3$, F, Cl, or Br;

$R^3$ is H, $CH_3$, $C_2H_5$, $C_2H_5$, $C_4H_9$, COOH, $COOCH_3$, $COOC_2H_5$, $COOC_2H_5$, or $COOC_4H_9$;

$R^4$ is H, $CH_3$, $C_2H_5$, $C_3H_7$, or $C_4H_9$;
X is NH, S, or O;
Z is $CH_2$, O, NH, or S;
i is 1 to 5;
j is 0 to 10;
k is 1 to 10;
m is 1-13; and
n is 1 to 15.

In another embodiment, this invention provides a method for stabilizing weight comprising chronic administration of an agent that stimulates CPT-1 activity in an amount that does not significantly inhibit FAS. In a preferred mode, the agent is administered in an amount sufficient to increase fatty acid oxidation. In another preferred mode, the agent is administered in an amount sufficient to antagonize malonyl CoA inhibition of CPT-1. In yet another preferred mode, the agent is administered in an amount sufficient to increase malonyl CoA level. In still another preferred mode, upon administration of the agent, malonyl CoA level is not substantially increased. Substantial increase in malonyl CoA level as contemplated herein is equivalent to about one-half the $K_i$ for malonyl CoA inhibition of CPT-1.

In still another embodiment, this invention provides a method of screening for agents that induce weight loss, comprising determining whether a candidate weight loss agent stimulates CPT-1 activity; and selecting an agent that stimulates CPT-1 activity. Preferably, this method further comprises determining whether the candidate weight loss agent is an antagonist of malonyl CoA inhibition of CPT-1, and candidate weight loss agents are selected that obviate malonyl CoA inhibition of CPT-1.

In yet another embodiment, this invention provides a therapeutic composition comprising an agent that stimulates CPT-1 activity and L-carnitine. Preferably, the therapeutic composition comprises an antagonist of malonyl CoA inhibition of CPT-1.

In still another embodiment, this invention provides a nutritional composition comprising nutritionally sufficient amounts of fats, carbohydrates and amino acids, said composition further comprising an antagonist of malonyl CoA inhibition of CPT-1 and L-carnitine. In one mode, the nutritional composition is adapted for parenteral administration.

To investigate the mechanism of action leading to the paradoxical reduction of fatty liver in the setting of high hepatic levels of malonyl-CoA during C75 treatment, the effect of C75 on CPT-1 activity was studied. Surprisingly, C75 and related compounds concomitantly stimulated CPT-1 activity and fatty acid oxidation in vitro while inhibiting FAS. In addition to its overall allosteric activation of CPT-1, C75 abrogated the inhibitory effect of malonyl-CoA on CPT-1 activity in vitro. As a consequence of increased fatty acid oxidation, C75 increased cellular ATP levels.

To test the effect of C75 on fatty acid oxidation in vivo, whole animal calorimetry was utilized to measure the respiratory exchange ratio (RER) in mice treated with C75. Following C75 therapy, the RER dropped within 2 h to the range of 0.7, indicative of fatty acid oxidation. This rate of RER decline was similar to food withdrawal from animals fed ad libitum with mouse chow. These studies indicate that, despite high hepatic levels of malonyl-CoA, C75 treated animals freely oxidized fatty acids.

These data suggest that C75 blocks the inhibitory action of malonyl-CoA on CPT-1 activity in vivo leading to a reduction in fatty liver and adipose mass during FAS inhibition. This invention describes a method to develop therapeutics that selectively reduce adiposity while preserving lean mass through the pharmacological stimulation of CPT-1 activity.

BRIEF DESCRIPTION OF THE FIGURES

FIG. 8 shows respiratory exchange ratio (RER) measured by indirect calorimetry for mice in the absence (A) and presence (B, C) of C75.

DETAILED DESCRIPTION OF PREFERRED EMBODIMENTS

Figure 1:
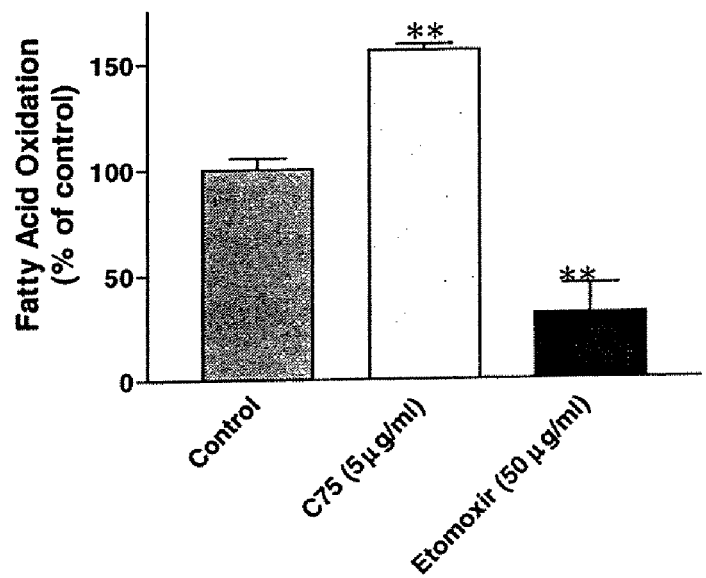
FIG. 1 shows the effect of C75 on fatty acid oxidation in MCF-7 cells, compared to the effect of Etomoxir.

Inhibition of fatty acid synthase (FAS) in vivo has been shown to cause rapid and profound weight loss. Both cerulenin, a natural product, and C-75, a synthetic small-molecule, cause similar weight loss when administered intracerebroventricularly (i.c.v.) to rats. When treated systemically (e.g., intraperitoneally), C-75 causes more profound weight loss, even weight loss greater than starved animals. These data demonstrate a greater peripheral (non-CNS) effect on weight loss for C-75 than for cerulenin.

While studying the mechanism of action of this profound peripheral effect of C-75, the inventors have recently found that in addition to inhibition of FAS, C-75 and its family of α-methylene-γ-butyrolactones, directly stimulates carnitine palmitoyltransferase-1 (CPT-1) leading to increased mitochondrial fatty acid oxidation. Cerulenin, in contrast, leads to reduced CPT-1 activity and reduced fatty acid oxidation through generation of high malonyl-CoA levels from FAS inhibition.

C75 treatment of MCF-7 cells in vitro stimulated CPT-I activity from 150-160%. There was also a concomitant increase in fatty acid oxidation. Among the C75 analogs, a carbon chain length of C6-C16 was optimum for CPT-1 stimulatory activity. In the presence of C75, malonyl-CoA is no longer able to inhibit CPT-1 activity, suggesting that in addition to its stimulatory effect, C75 also prevents malonyl-CoA inhibition of CPT-1. There is no detectable covalent interaction between CPT-1 and C75.

Thus, the peripheral (non-CNS) weight loss effect of C-75 is at least in part due to CPT-1 stimulation and increased fatty acid oxidation with concomitant fatty acid synthesis inhibition. These data identify a family of α-methylene-γ-butyrolactones as malonate or malonyl-CoA mimetics and CPT-1 as a target for weight loss therapeutics and. More broadly, our data suggest that other malonate or malonyl-CoA mimetics can be designed and synthesized to function as effective weight loss agents.

Data demonstrate that C-75 and its family of α-methylene-γ-butyrolactones directly interact with CPT-1 leading to increased CPT-1 enzymatic activity and fatty acid oxidation. The chemical structure of C75 and numerous analogs, as well as methods of synthesizing these analogs, are disclosed in U.S. Pat. No. 5,981,575, which is incorporated herein by reference. The stimulatory effect of C75 is related to the length of the saturated carbon side chain, with the optimum length between 6-18 carbon atoms. With regard to the discussion of the present invention, C75 is the prototype agent for stimulation of CPT-1; reference to C75 hereinafter includes other suitable agents which stimulate CPT-1 activity, except where indicated otherwise by context. Other suitable agents which stimulate CPT-1 activity include a variety of gamma-butyrolactones which can be readily identified by testing the effect on CPT-1 activity of gamma-substituted-alpha-methylene-butyrolactones, such as those described in International Patent Publication WO 2004/006835, incorporated herein by reference, substituted thiotetronic acids, such as those described in International Patent Publication WO 2004/005277, incorporated herein by reference, and substituted thiophene diones described in U.S. Provisional Patent Application 60/574,639, incorporated herein by reference.

In addition to its direct effect upon CPT-1, C-75 abolishes the inhibitory effect of malonyl-CoA on CPT-1 activity. Although C75 exhibits kinetic features of a slow-binding inhibitor with purified FAS (1), its interaction with CPT-1 appears rapid and competitive. Thus, the stimulatory effect of C75 upon fatty acid oxidation may be due to either its direct stimulation of CPT-1 activity, its interference of malonyl-CoA inhibition of CPT-1, or both. Interestingly, the effects of C75 are not restricted to murine CPT-1, as human CPT-1 was similarly affected. As a consequence of increased fatty acid oxidation, C75 also increased ATP levels in both the human and murine cells.

The effect of C75 on fatty acid metabolism in vivo mirrored the alterations seen on a cellular level. C75 treatment of lean mice led to a profound and rapid increase in fatty acid oxidation, despite the high levels of malonyl-CoA generated by C75 in vivo. Thus, C75 and its family of α-methylene-γ-butyrolactones, appear to act as competitive agonists of CPT-1. This agonist activity of C75 appears to overcome inhibitory effects of malonyl CoA on the same enzyme. The increased fatty acid oxidation induced by C75 is an important mechanism accounting for marked reduction in adiposity seen during C75 treatment of mice.

In summary, this invention describes a method to develop therapeutics that selectively enhance fatty acid oxidation, increase energy production, and reduce adiposity while preserving lean mass, through the pharmacological stimulation of CPT-1 activity.

Formulation of therapeutic compositions containing C75 and/or other agents that stimulate CPT-1, and methods of administering such agents, are within the skill of the art, particularly in view of the description in U.S. Pat. No. 5,981,575, the text of which is incorporated herein by reference.

Use of CPT-1 stimulating agents to increase energy production by administering the agents contemporaneously with fatty acids or compounds containing fatty acid residues is also within the skill of the art, particularly in view of the nutritional compositions disclosed in U.S. Pat. No. 4,434,160, the text of which is incorporated herein by reference.

EXAMPLES

In order to facilitate a more complete understanding of the invention, a number of Examples are provided below. However, the scope of the invention is not limited to specific embodiments disclosed in these Examples, which are for purposes of illustration only.

Example 1

Paradoxical Effects of a Fatty Acid Synthase Inhibitor

Cerulenin, an FAS inhibitor, increases malonyl-CoA amount in MCF-7 cells (3). As a consequence of the massive increase in malonyl-CoA, cerulenin causes inhibition of fatty acid oxidation through the malonyl-CoA inhibition of CPT-1 (Thupari, et al. (2001) *Biochem. Biophys. Res. Comm.*, 285: 217-223). Previously, it was shown that C75 treatment of MCF-7 cells resulted in a >5-fold increase in malonyl-CoA through C75 inhibition of fatty acid synthase (FAS) (3). The effect of C-75 on fatty acid oxidation was tested as follows.

Human breast cancer cell line MCF-7 was obtained from the American Type Culture Collection. $1 \times 10^6$ MCF-7 cells were plated in T-25 flasks in triplicate and incubated overnight at 37° C. Drugs were then added as indicated diluted from 5 mg/ml stock in DMSO. After 2 hours, medium with drugs was removed and cells were preincubated for 30 min. with 1.5 ml of the following buffer: 114 mM NaCl, 4.7 mM KCl, 1.2 mM $KH_2PO_4$, 1.2 mM $MgSO_4$, glucose 11 mM. After preincubation, 200 µl of assay buffer was added containing: 114 mM NaCl, 4.7 mM KCl, 1.2 mM $KH_2PO_4$, 1.2 mM $MgSO_4$, glucose 11 mM, 2.5 mM palmitate (containing with 10 µCi of [1-$^{14}$C]palmitate) bound to albumin, 0.8 mM L-carnitine, and cells were incubated at 37° C. for 2 h. Following the incubation, 400 µl of benzethonium hydrochloride was added to the center well to collect released $^{14}CO_2$. Immediately, the reaction was stopped by adding 500 µl of 7% perchloric acid to the cells. The flasks with wells were then incubated for 2 h at 37° C. after which the benzothonium hydrochloride was removed and counted for $^{14}$C. Blanks were prepared by adding 500 µl of 7% perchloric acid to the cells prior to the incubation with the assay buffer for 2 h.

When cells were treated with C75 2 hours before fatty acid oxidation was measured, C75 treatment resulted in a 156% increase in fatty acid oxidation compared to the control (see FIG. 1; p=0.0012, two-tailed t-test, Prism 3.0). In contrast, Etomoxir, a known inhibitor of fatty acid oxidation and non-competitive inhibitor of CPT-1, decreased fatty acid oxidation to 32% of control (p=0.0006, two-tailed t-test, Prism 3.0). C-75 treatment of MCF-7 cells repeatedly resulted in increased fatty acid oxidation with doses from 5-20 µg/ml.

Paradoxically, despite an increase in malonyl-CoA similar to that induced by cerulenin, C75 treatment increased rather than decreased fatty acid oxidation in MCF-7 cells. This implies a direct effect of C75 upon carnitine palmitoyltransferase-1 (CPT-1).

Example 2

C75 Stimulates Activity of Human CPT-1

CPT-1 activity was assayed in MCF-7 cells by the following published procedure: MCF-7 cells were plated in DMEM with 10% fetal bovine serum at $10^6$ cells in 24-well plates in triplicate. Following overnight incubation at 37° C., the medium was removed and replaced with 700 µl of assay medium consisting of: 50 mM imidazole, 70 mM KCl, 80 mM sucrose, 1 mM EGTA, 2 mM $MgCl_2$, 1 mM DTT, 1 mM KCN, 1 mM ATP, 0.1% fatty acid free bovine serum albumin, 70 µM palmitoyl-CoA, 0.25 µCi [methyl-$^{14}$C]L-carnitine, 40 µg digitonin with or without 20 µM malonyl-CoA. After incubation for 6 minutes at 37° C., the reaction was stopped by the addition of 500 µl of ice-cold 4 M perchloric acid. Cells were then harvested and centrifuged at 13,000×g for 5 min.

The pellet was washed with 500 μl ice cold 2 mM perchloric acid and centrifuged again. The resulting pellet was resuspended in 800 μl dH$_2$O and extracted with 150 μl of butanol. The butanol phase was counted by liquid scintillation and represents the acylcarnitine derivative.

MCF-7 cells were treated with C75 at 10 or 20 μg/mL for 1 hr before CPT-1 activity was assayed. The assay was performed with the C75 and malonyl-CoA concentrations indicated ("M" indicates malonyl-CoA at 20 uM). Malonyl-CoA treatment alone caused a 46% reduction in CPT-1 activity similar to the previous experiment (see FIG. 2; p=0.02, two-tailed t-test, Prism 3.0). The level of malonyl-CoA inhibition of the CPT-1 activity is consistent with the activity of the liver isoform of CPT-1 in MCF-7 cells. The $K_i$ of malonyl-CoA for the liver isoform of CPT-1 is ~7 μM while the $K_i$ for the muscle isoform of CPT-1 is 0.07 μM. Thus, MCF-7 cells express predominantly the liver isoform of CPT-1 (consistent with the immunoblot analysis).

Figure 2:
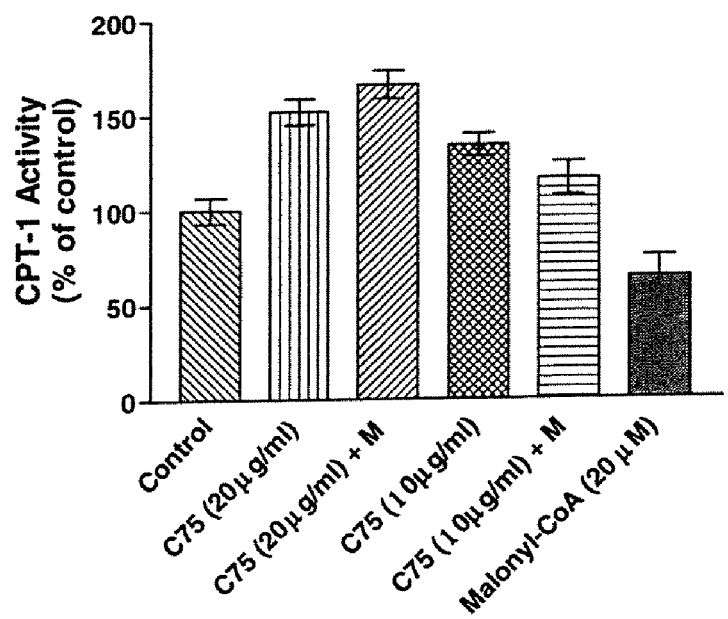
FIG. 2 shows concentration dependent stimulation of CPT-1 activity by C75 and inhibition by malonyl CoA.

There was no statistically significant difference in CPT-1 activity between cells treated with C75 or C75 and malonyl-CoA (FIG. 2). Thus, in the presence of C75, malonyl-CoA lost its inhibitory effect on CPT-1; conversely, C75 stimulation of CPT-1 occurred regardless of the presence of malonyl-CoA. Thus, in the presence of C75, the normal inhibitory activity of malonyl-CoA is lost. Malonyl-CoA inhibition of CPT-1 activity demonstrated that C75 and related compounds were activating CPT-1 rather than CPT-2 activity which is not inhibitable by malonyl-CoA.

Figure 3:
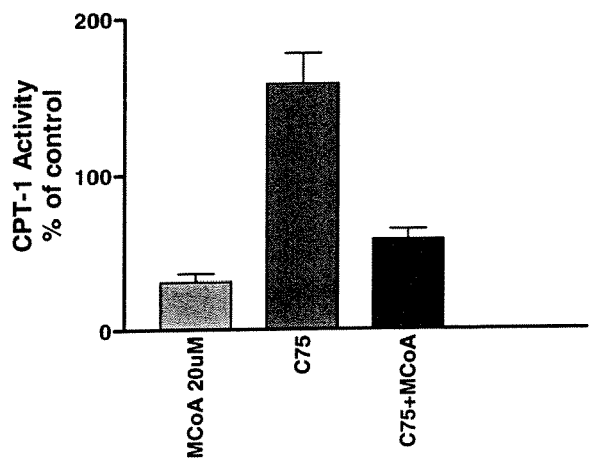
FIG. 3 shows reversible stimulation of CPT-1 by C75.

In a subsequent experiment (data in FIG. 3), MCF-7 cells were untreated (left bar) or treated with C75 at 20 μg/ml for one hour before CPT-1 activity was measured (middle and right bars). During the 6 minutes of the CPT-1 assay, C75 was removed from the assay buffer and replaced with buffer (middle bar) or malonyl-CoA 20 μM was added (left & right bars). Malonyl-CoA treatment alone during the assay resulted in a ~70% inhibition of CPT-1 activity (left bar) (p=0.0045, two-tailed t-test, Prism 3.0). Prior C75 treatment with no C75 in the assay buffer resulted in CPT-1 activity of 158% of control (p=0.028, two-tailed t-test, Prism 3.0), similar to the results when C75 is kept in the assay buffer (see above experiment). However, when C75 is removed from the reaction buffer and malonyl-CoA is replaced, C75 stimulatory activity is lost (right bar). Thus, C-75 does not detectably bind covalently to CPT-1, and it is likely a competitive antagonist with malonyl-CoA. These data also suggest that C-75 interacts with CPT-1 at the malonyl-CoA binding site.

Example 3

Structure of Effective CPT-1 Stimulators

Figure 4:
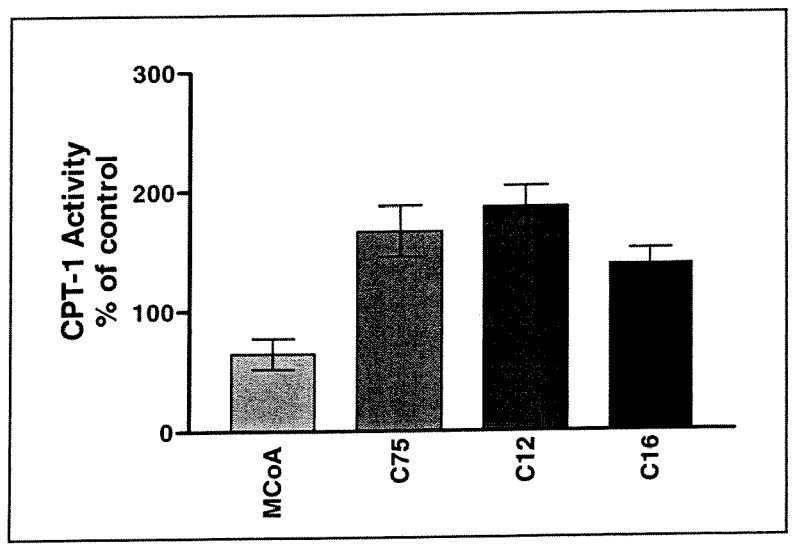
FIG. 4 shows stimulation of CPT-1 by various C75 analogs.

Analogs of α-methylene-γ-butyrolactones differing only in the length of their saturated carbon 'tail' were prepared as described in U.S. Pat. No. 5,981,575, incorporated herein by reference. C75 has an eight-carbon tail, C12 and C16 have tails of 12 and 16 carbons respectively. Cells were treated with C75 and C75 analogs at 20 μg/ml 1 hr before CPT-1 activity was measured. Malonyl-CoA was added only to the reaction buffer since the whole cell is impermeable to malonyl-CoA. C75 stimulated CPT-1 activity to 166% of control at a dose of 20 μg/ml (see FIG. 4; p=0.0092, two-tailed t-test, Prism 3.0). C12 analog stimulated to 186% (p=0.0099, two-tailed t-test, Prism 3.0) and C16 analog stimulated to 138% of control (p=0.055, two-tailed t-test, Prism 3.0). Malonyl-CoA, an intracellular competitive inhibitor of CPT-1, reduced CPT-1 activity to 64% of control at 20 μM (p=0.023, two-tailed t-test, Prism 3.0). The optimum carbon chain length for CPT-1 activation is between 6 and 16 carbons.

Example 4

Enhanced Fatty Acid Oxidation from CPT-1 Stimulation Produces ATP

Figure 5:
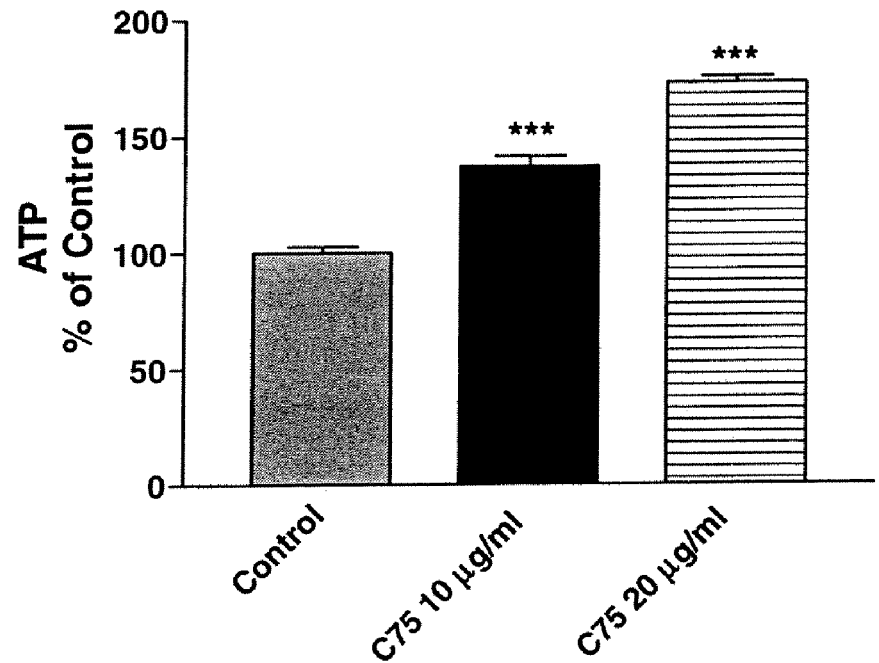
FIG. 5 shows concentration dependent enhancement of cellular ATP levels by C75 in MCF-7 cells.

As a consequence of increased fatty acid oxidation, ATP was elevated in MCF-7 cells following C75 treatment. $1 \times 10^5$ MCF-7 cells were plated in 96 well plates. Cells were treated with C75 or vehicle. After 2 hours, ATP was measured using a luciferase assay using the ATP Bioluminescence Kit CLS II (Roche) following the manufacturer's protocol. Plates were read by a Perkin Elmer Wallac Victor$^2$ 1420 luminometer. C75 treatment at 10 μg/ml and 20 μg/ml both resulted in a significant increase in total cellular ATP (see FIG. 5; p=0.0001; p<0.0001 compared to control, two-tailed t-test, Prism 3.0). Similar results were obtained after 1 hr incubation with C75. Thus, cellular energy production increased as a result of C75 increasing fatty acid oxidation.

Example 5

C75 Stimulates Activity of Muscle Form CPT-1

To expand the study of effects of C75 on fatty acid metabolism beyond cancer cell lines to normal adipocytes, differentiated (non-transformed) mouse NIH 3T3-L1 adipocytes were used in assays similar to those performed with the MCF-7 cells. 3T3-L1 cells were obtained from the American Type Culture Collection, and cells were cultured in DMEM with high glucose (4.5 g/l) (Gibco 12100-046) with 10% fetal calf serum and Biotin (Sigma B-4639) 0.008 g/L. Differentiation was initiated three days after the cells were confluent, when the standard culture medium was replaced with differentiation medium. The differentiation medium contained standard culture medium to which the following were added to achieve the final concentrations: methylisobutylxanthine (MIX) 0.5 mM, dexamethasone (DEX) 1 μM, and insulin 10 μg/ml. After 48 hrs, the differentiation medium was replaced with post-differentiation medium which contained insulin at the above concentration, without MIX and DEX. The differentiated cells were ready to be used for experiments in 7-10 days.

Figure 6:
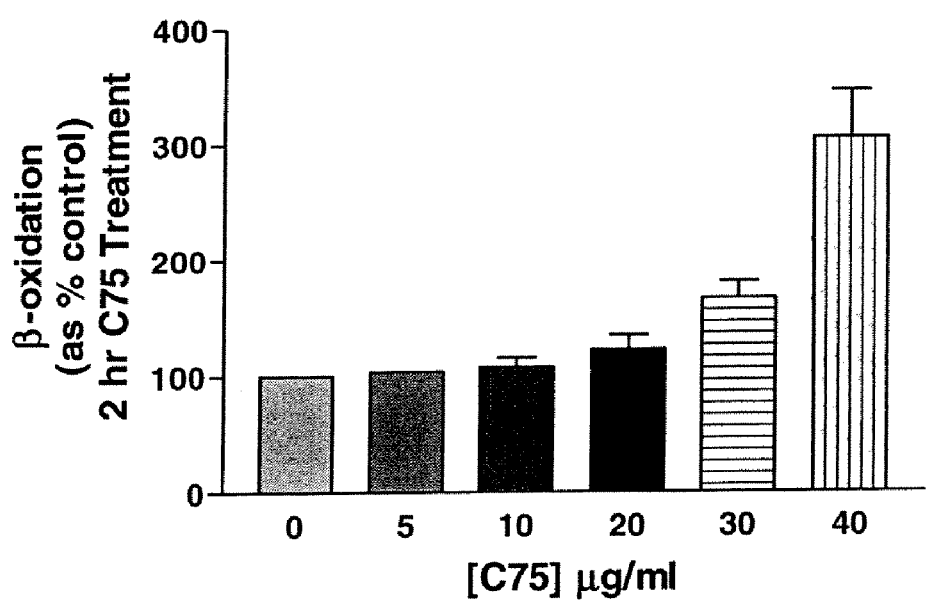
FIG. 6 shows concentration dependent stimulation of fatty acid oxidation by C75 in mouse adipocytes.
Figure 7:
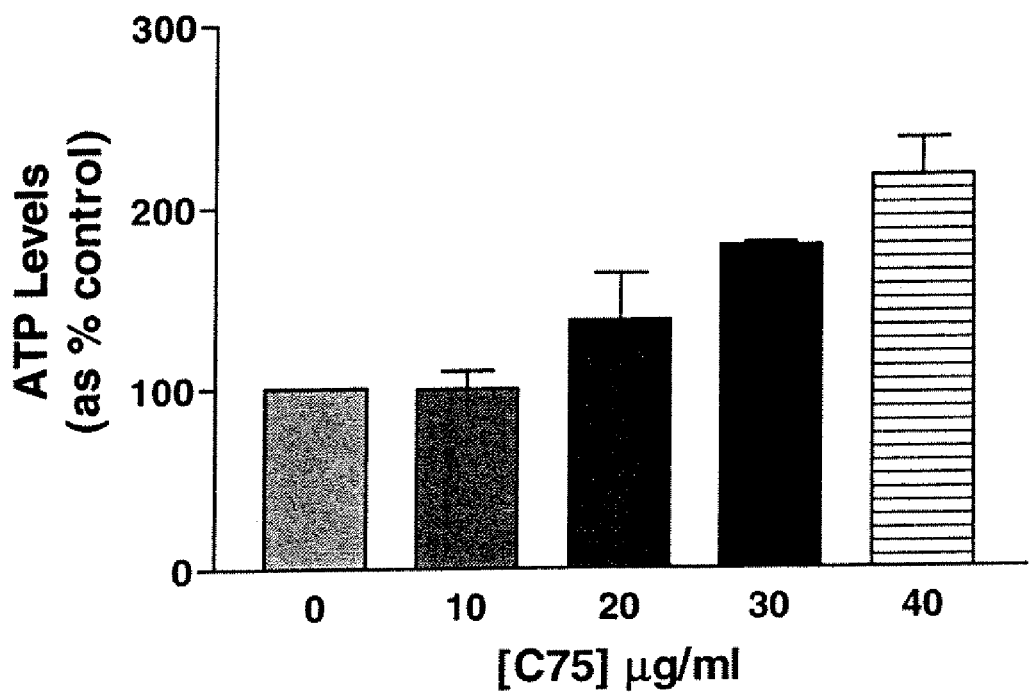
FIG. 7 shows concentration dependent enhancement of cellular ATP levels by C75 in mouse adipocytes.

C75 increased CPT-1 activity and fatty acid metabolism in the NIH 3T3-L1 cells differentiated into adipocytes. One week post differentiation, cells were treated with either vehicle control or C75 for 2 hours at doses indicated below. CPT-1 activity, fatty acid oxidation, and total cellular ATP were measured as described in Examples 2, 1, and 4. C75 treatment of 3T3-L1 adipocytes led to a 377% increase in CPT-1 activity above control (p<0.0001, two-tailed t-test, Prism 3.0). As a consequence of increased CPT-1 activity, C75 at doses of 20 μg/ml or greater, significantly increased fatty acid oxidation (see FIG. 6; 20 μg/ml, p=0.007; <20 μg/ml, p<0.0001; two-tailed t-test, Prism 3.0). Moreover, the increase in fatty acid oxidation led to significantly increased levels of ATP at C75 doses of 20 μg/ml or greater (see FIG. 7; 20 μg/ml, p=0.05; 30 μg/ml, p<0.01; 40 μg/ml, p<0.0001; two-tailed t-test, Prism 3.0). The enhanced fatty acid oxidation induced by C75 is likely responsible for the marked reduction in adipose tissue mass seen with C75 administration in vivo.

Example 6

In vivo Stimulation of CPT-1 Shifts Metabolism to Fatty Acid Oxidation

In keeping with the C75 effect on both human and murine CPT-1 and fatty acid metabolism, C75 induces a profound and rapid stimulation of fatty acid oxidation in vivo. Mice were maintained in the Oxymax calorimeter (Oxymax Equal Flow System®, Columbus Instruments, Columbus, Ohio). Oxygen consumption and $CO_2$ production was measured in up to four mice simultaneously using the indirect calorimeter. Measurements were recorded every 15 minutes over the entire course of the experiments. The respiratory exchange ratio (RER) was calculated by the Oxymax® software version 5.9. RER is defined as the ratio of $CO_2$ to $O_2$ at any given time irrespective if equilibrium was reached. Mice were maintained on water and mouse chow ad libitum. In the control mice (FIG. 8A), note the diurnal variation of RER indicating feeding and resting cycles of the animals. An RER of 1 is consistent with oxidation of carbohydrates while 0.7 indicates oxidation of fatty acids. Mice treated with C75 and maintained in the Oxymax calorimeter showed a rapid decrease in the respiratory exchange ratio (RER) to ~0.7 (FIG. 8B). C75 treatment at 30 mg/kg disrupts the diurnal pattern of the control mice, showing a rapid drop in RER to complete oxidation of fatty acids within about 2 hours. Similarly, C75 treatment at 20 mg/kg shows a similar rate of drop of RER but without the prolonged effect (FIG. 8C). Importantly, the rate of decline of RER was similar to that observed for animals deprived of food (data not shown).

Despite the elevated levels of malonyl-CoA generated by C75 in vivo, C75 treatment led to a rapid, profound increase in fatty acid oxidation as measured by RER. Thus, C75 treated animals are able to significantly reduce adipose mass and reverse fatty liver, by allowing fatty acid oxidation to occur despite the high levels of malonyl-CoA generated during FAS inhibition in vivo.

Example 7

Enzyme Effector Activity of Various Substituted Gamma-Butyrolactones

Various gamma-butyrolactone analogs were prepared and tested for their effect on FAS activity, CPT-1 activity and fatty acid oxidation. The compounds included C-75, a gamma-substituted-alpha-methylene-butyrolactone synthesized as described in U.S. Pat. No. 5,981,575, FAS231 and FAS65, gamma-substituted-alpha-methylene-beta-amido-butyrolactones, synthesized as described in International Pat. Publication WO 2004/006835, FAS115, a 5,5-disubstituted thiotetronic ethyl carbonate synthesized as described in International Patent Publication WO 2004/005277, and FAS89B, an 3,3,5,5-tetrasubstitued thiophene dione, synthesized as described in U.S. Provisional Patent Application 60/574,639. CPT-1 and fatty acid oxidation, and the results of the assays are shown in the following table.

FAS activity was measured by monitoring the malonyl-CoA dependent oxidation of NADPH spectrophotometrically at $OD_{340}$ in 96-well plates, as described in International Patent Publication WO 2004/005277. The $IC_{50}$ for the compounds against FAS was determined by plotting the change in $OD_{340}$ against time for each inhibitor concentration tested and determining the rate of change by linear regression. The concentration of a particular compound yielding 50% inhibition of the rate for FAS in the absence of the compound is the $IC_{50}$. Stimulation of CPT-1 activity was measured as described in Example 2, except the cells were preincubated with the compound for 2 hours at the concentrations indicated in the table. Stimulation of Fatty acid oxidation was determined as described in Example 1 for cells preincubated with the compounds at the concentrations indicated in the table.

TABLE

Effect of Selected Compounds on Enzyme Activities

| Compound | FAS Inhibition ($IC_{50}$) µg/mL | CPT-1 Stimulation µg/mL | CPT-1 Stimulation (% Control) | Fatty Acid Oxidation µg/mL | Fatty Acid Oxidation (% Control) |
|---|---|---|---|---|---|
| C75 | 55 | 20 | 125 | 10 | 400 |
| 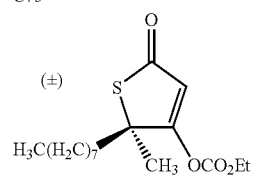 FAS 115 | 4.6 | 20 | 150 | 10 | 140 |
| 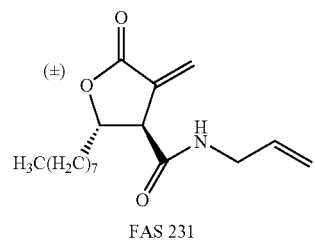 FAS 231 | 47.9 | 10 | 400 | 0.625 | 400 |

TABLE-continued

Effect of Selected Compounds on Enzyme Activities

| Compound | FAS Inhibition (IC$_{50}$) μg/mL | CPT-1 Stimulation | | Fatty Acid Oxidation | |
|---|---|---|---|---|---|
| | | μg/mL | (% Control) | μg/mL | (% Control) |
| 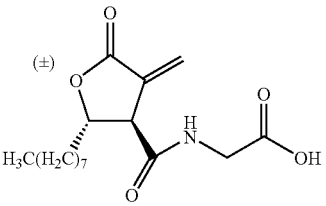 FAS 65 | 52.1 | 80 | 500 | 40 | 500 |
| 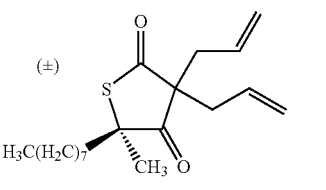 FAS 89B | n/a* | 20 | 175 | 10 | 175 |

*Slow binding assays not yet completed

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All such publications and patent applications are herein incorporated by reference to the same extent as if each individual publication or patent application was specifically and individually indicated to be incorporated by reference.

The invention claimed is:

1. A method of inducing weight loss comprising administering to a patient an effective amount of an agent that stimulates carnitine palmitoyl transferase-1 (CPT-1) activity in an amount that does not significantly inhibit FAS.

2. A method for stabilizing weight comprising chronic administration to a patient of an effective amount of an agent that stimulates CPT-1 activity in an amount that does not significantly inhibit FAS.

3. A method of screening for agents that induce weight loss, comprising determining whether a candidate weight loss agent stimulates CPT-1 activity in an amount that does not significantly inhibit FAS; and selecting an agent that stimulates CPT-1 activity in an amount that does not significantly inhibit FAS.

* * * * *